(12) United States Patent
Kirkbride et al.

(10) Patent No.: US 8,260,578 B2
(45) Date of Patent: *Sep. 4, 2012

(54) METHOD OF DETERMINING THE DYNAMIC LOCATION OF A PROTECTION

(75) Inventors: Tana Marie Kirkbride, Cincinnati, OH (US); Thomas Ward Osborn, III, Cincinnati, OH (US); Reginald Edward Crutcher, II, Cincinnati, OH (US); Marie Brigid O'Reilly, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1143 days.

This patent is subject to a terminal disclaimer.

(21) Appl. No.: 12/123,032

(22) Filed: May 19, 2008

(65) Prior Publication Data

US 2009/0284592 A1 Nov. 19, 2009

(51) Int. Cl.
G06F 15/02 (2006.01)
(52) U.S. Cl. ............ 702/187; 702/94; 702/95; 702/127; 702/150; 702/153; 604/317; 116/209
(58) Field of Classification Search .................. 702/150; 348/94
See application file for complete search history.

(56) References Cited

U.S. PATENT DOCUMENTS

| | | | | |
|---|---|---|---|---|
| 5,676,673 | A * | 10/1997 | Ferre et al. | 606/130 |
| 6,702,736 | B2 | 3/2004 | Chen et al. | |
| 6,753,783 | B2 * | 6/2004 | Friedman et al. | 340/573.7 |
| 6,941,239 | B2 * | 9/2005 | Unuma et al. | 702/141 |
| 7,653,508 | B1 * | 1/2010 | Kahn et al. | 702/160 |
| 2003/0163287 | A1 * | 8/2003 | Vock et al. | 702/187 |
| 2004/0106202 | A1 * | 6/2004 | Zainiev et al. | 436/39 |
| 2006/0069536 | A1 | 3/2006 | Butsev et al. | |
| 2006/0183993 | A1 * | 8/2006 | Horn | 600/407 |
| 2007/0208542 | A1 * | 9/2007 | Vock et al. | 702/187 |
| 2008/0094226 | A1 * | 4/2008 | O'Shea et al. | 340/573.1 |
| 2008/0183450 | A1 * | 7/2008 | Macura et al. | 703/9 |
| 2008/0269596 | A1 | 10/2008 | Revie et al. | |
| 2008/0287781 | A1 | 11/2008 | Revie et al. | |
| 2009/0043531 | A1 * | 2/2009 | Kahn et al. | 702/149 |
| 2009/0284592 | A1 * | 11/2009 | Kirkbride et al. | 348/94 |
| 2009/0287454 | A1 * | 11/2009 | Osborn et al. | 702/187 |

FOREIGN PATENT DOCUMENTS

| | | |
|---|---|---|
| GB | 2 430 117 A | 3/2007 |
| JP | 2001052202 A | 2/2001 |
| WO | WO 2006/092600 A1 | 9/2006 |

OTHER PUBLICATIONS

PCT International Search Report dated Aug. 9, 2009.

(Continued)

*Primary Examiner* — Jonathan C Teixeira Moffat
*Assistant Examiner* — Timothy H Hwang
(74) *Attorney, Agent, or Firm* — Andrew J. Hagerty; Amanda T. Barry

(57) ABSTRACT

The method uses a location device and a timing element to determine the location of a protection device at various periods of time. During these periods of time, the human may be participating in a variety of activities and positions.

10 Claims, 5 Drawing Sheets

OTHER PUBLICATIONS

Lasse Klingbeil et al.: "A Wireless Sensor Network for Real-Time Indoor Localisation and Motion Monitoring" Information Processing in Sensor Networks, 2008. IPSN '08. International Conference ON, IEEE, Piscataway, NJ, USA, Apr. 22, 2008, pp. 39-50.

Dirk Ahlers et al. "GNSS quality in pedestrian applications—a eveloper perspective" Positioning, Navigation and Communication, 2008. WPNC 2008, $5^{th}$ Workshop ON, IEEE, Piscataway, NJ, USA, Mar. 27, 2008, pp. 45-54.

* cited by examiner

US 8,260,578 B2

METHOD OF DETERMINING THE DYNAMIC LOCATION OF A PROTECTION

BACKGROUND OF THE INVENTION

This Background is intended to provide the basic context of this patent application and it is not intended to describe a specific problem to be solved.

Protection devices, such as tampons, diapers, feminine pads, etc., have existed for several years. Protection devices are created in such a manner to attempt to cover as many positions and activities of a person as possible. However, how the protection device will react to the movements and activities of a person can be a matter of conjecture.

Attempts have been made to study the position of protection devices worn by a user. These attempts have been limited, as monitoring methods such as MRI and ultrasound typically allow for no or only limited movement of the user. As a result, previous attempts have been unable to observe the dynamic movement of a protection device worn by a user while the user moves through various activities and/or body movements common in their daily lives. In addition, it has been virtually impossible to correlate users' sensory perceptions related to the protection device with the actual position of the protection device relative to a human body.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A method and user interface for monitoring the dynamic movement of a protection device worn by a human being is provided. The method uses a location device and a timing element to determine the location of a protection device at various periods of time. During these periods of time, the human may be participating in a variety of activities and positions, all of which may be stored and studied in real time or at a later time. As a result, the locations of a protection device may be illustrated on a user interface.

DETAILED DESCRIPTION OF THE INVENTION

Although the following text sets forth a detailed description of numerous different embodiments, it should be understood that the legal scope of the description is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Figure 1:
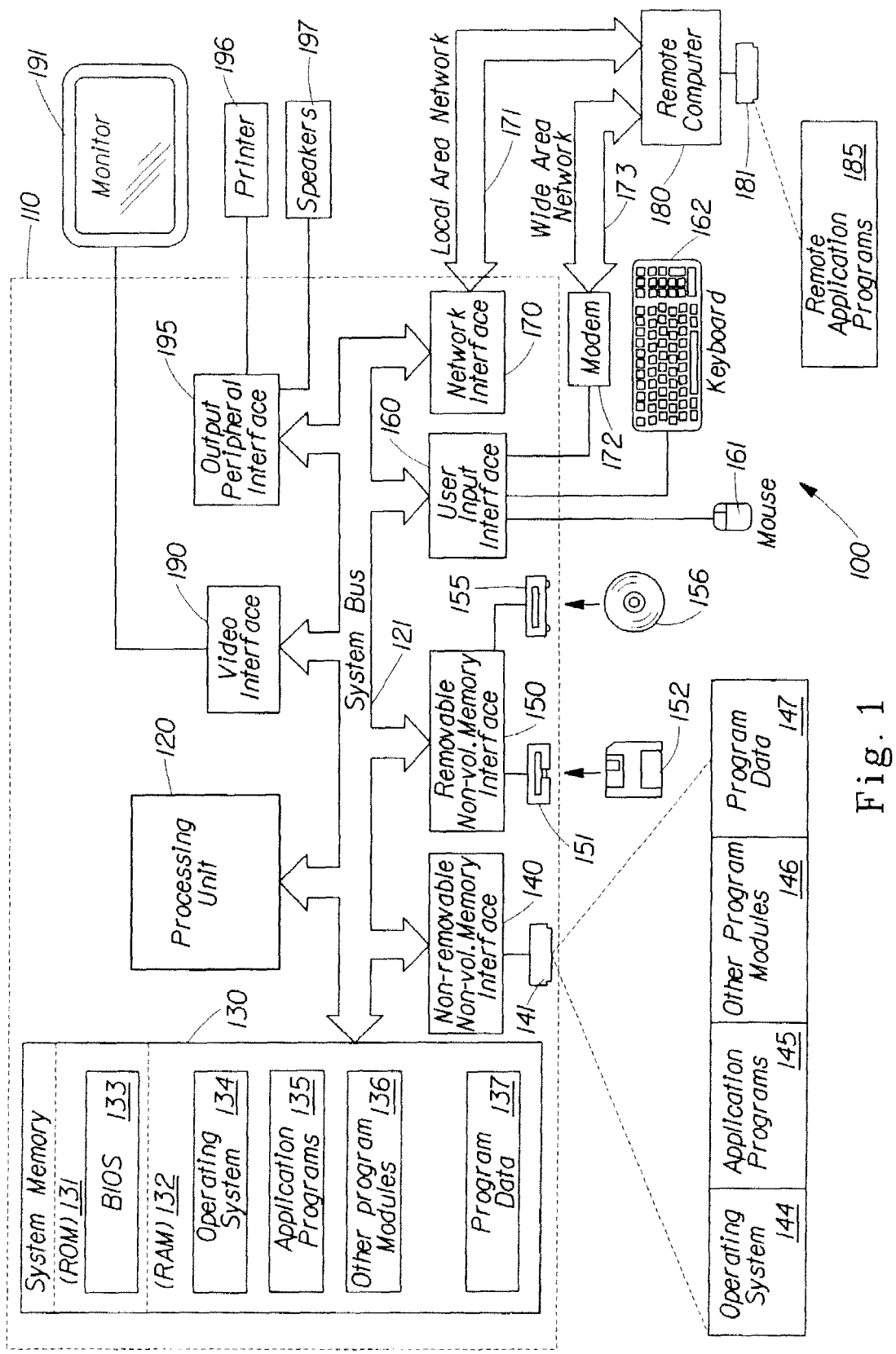
FIG. 1 is a block diagram of a computing system that may operate in accordance with the claims.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and apparatus are operational with numerous other general purpose or special purpose computing system environments or configurations. Examples of well known computing systems, environments, and/or configurations that may be suitable for use with the methods or apparatus of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method, the user interface and apparatus may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the steps of the claimed method and apparatus includes a general purpose computing device in the form of a computer 110. Components of computer 110 may include, but are not limited to, a processing unit 120, a system memory 130, and a system bus 121 that couples various system components including the system memory to the processing unit 120. Computer 110 typically includes a variety of computer readable media. Computer readable media can be any available media that can be accessed by computer 110 and includes both volatile and nonvolatile media, removable and non-removable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Figure 2:
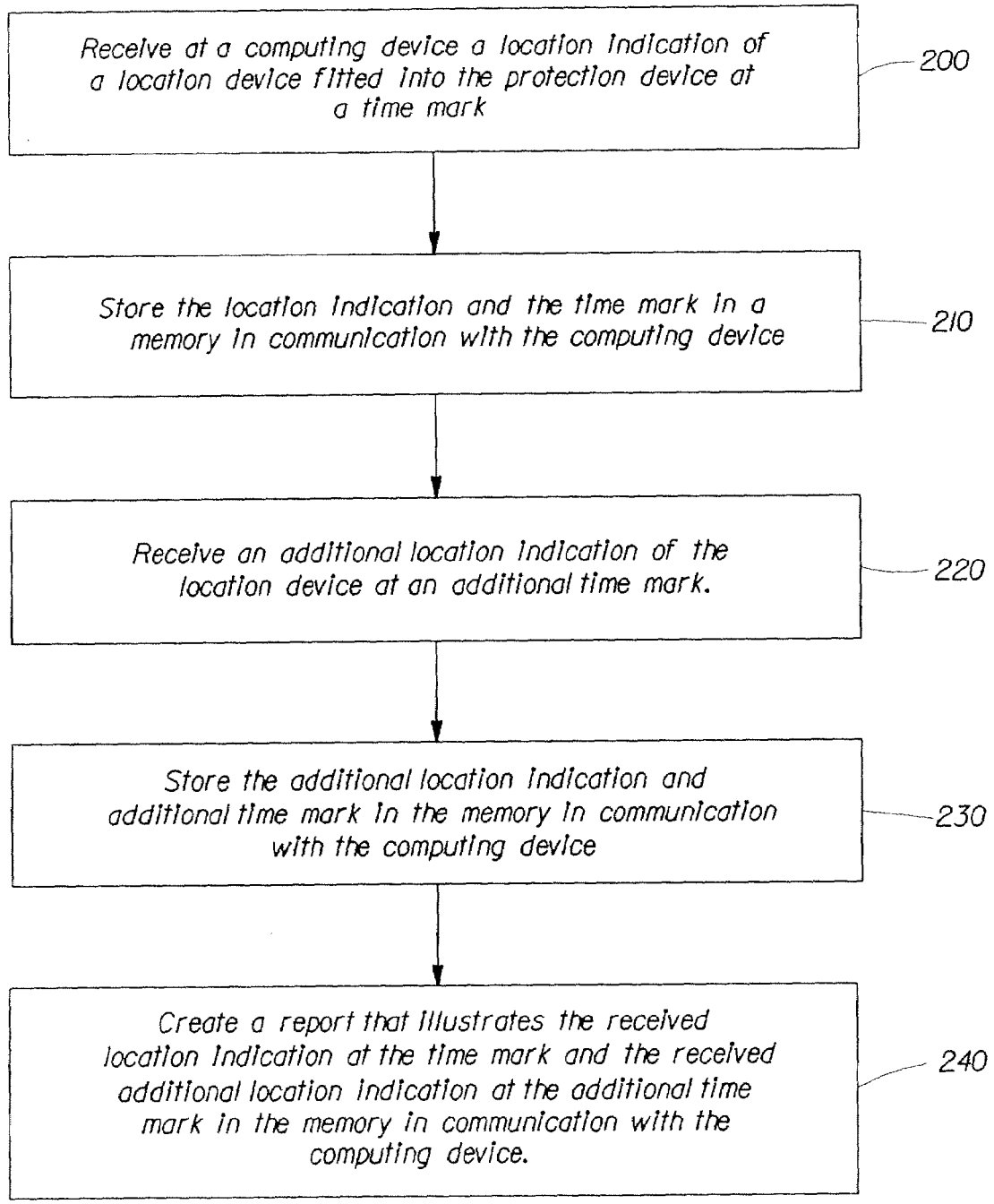
FIG. 2 is a flowchart of a method of obtaining dynamic data related to a protection device worn inside clothing on a human being during one or more body movements.

FIG. 2 illustrates a method of obtaining dynamic data related to a protection device worn by a human being during one or more body movements. The protection device can be worn in any suitable manner, such as, e.g., on or in the human being. In certain embodiments, the protection device can be worn inside clothing on a human being. The method may include a computer application that is executed on a computer, such as the computer 100 described in FIG. 1, or in any other computing device capable of executing computer executable code.

Figure 3:
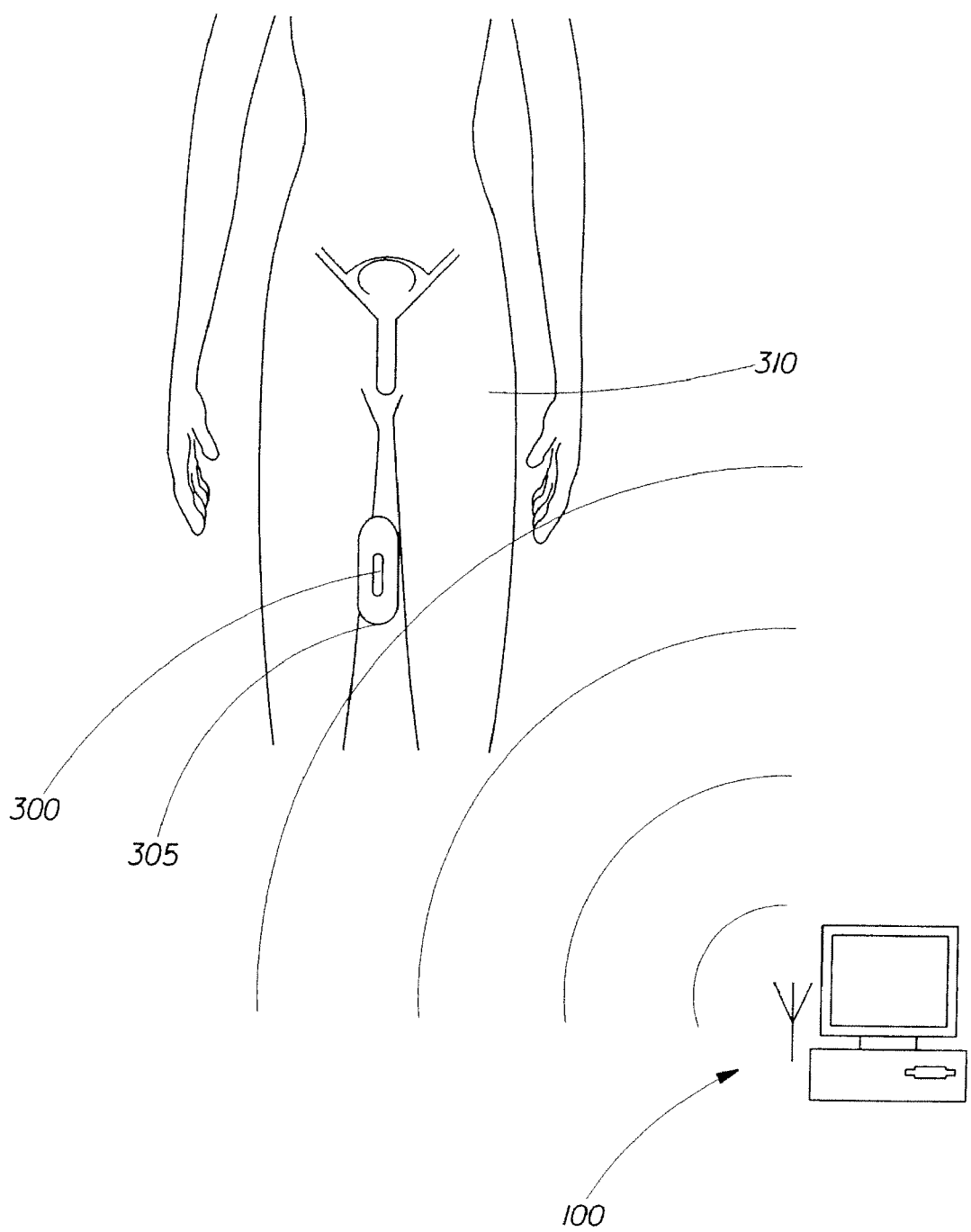
FIG. 3 is an illustration of a location device associated with a protection device and a computer with a memory.

At block 200, the computing device 100 may receive a location indication of a location device associated with the protection device at a time mark. FIG. 3 is an illustration of one location device 300 associated with a protection device 305. The location device 300 may be fitted inside, outside or a combination of inside and outside of a protection device 305.

The protection device 305 may be, for example and not limitation, an absorbent article, such as, e.g., a tampon, a sanitary pad, a pessary device, an incontinence pad, a pantiliner, an interlabial device, or a diaper; a feminine product, such as, e.g., a tampon, a sanitary pad, an incontinence pad, a pantiliner, an interlabial device, a diaper, a pessary, a diaphragm, a cervical cap, a contraceptive sponge, or a contraceptive ring; and/or a vaginal device, such as, e.g., a tampon, a pessary, a diaphragm, a cervical cap, a contraceptive sponge, or a contraceptive ring. In certain embodiments, the protection device 305 may be a bandage or a heat wrap.

In certain embodiments, the location device 300 may be associated with the protection device, such as, e.g., fitted, for example and not limitation, as part of the protection device, such as, e.g., as part of an absorbent core of a pad, a topsheet of a pad, wings of a pad, a withdrawal member of a tampon, a secondary absorbent member of a tampon, an elastic barrier on an incontinent product or diaper, a waist band elastic barrier on an incontinent product or diaper, or a leg elastic barrier on an incontinent product or diaper. The location device 300 also may be associated with, such as, e.g., fitted to an undergarment. The protection device 305 may be for males, females or for other animals that use protection devices 305.

The location device 300 may be of a size such that movement of the human being is not inhibited by the location device 300. For example and not limitation, the location device 300 may be less than 3 cm in length, less than 0.5 cm in diameter and may have a surface area less than 3 cm square.

The location device 300 may create a location indication. The location indication may be used by the computer application such as computer application 135 (FIG. 1) to interpret the actual location of the location device 300. The location indication may indicate the location of the location device 300 in comparison to another, known fixed point or may be in comparison to the body of the person 310 being studied. In another embodiment, GPS signals are used to create a location indication.

Time marks may be used to establish a time at which location indications are received. By tracking the location indication over a plurality of time marks or points in time, the movement of the location device 300 may be created. In addition, the time mark may by synchronized with other timing devices such as the timing device in the computer 100 such that other factors may be matched to the location indication at the same time mark. For example, a subject may feel wetness at a time mark A. The computer system may then examine the location of the protection device 305 at the time the wetness feeling occurred (time mark A). Synchronizing time among a plurality of computing devices may be accomplished in a variety of ways, all of which are contemplated. For example and not limitation, clocks in the location device 300 and the computing device 100 may be synchronized before location indication is communicated. Other embodiments are possible and are contemplated.

At block 210, the location indication and the time mark may be stored in a memory in communication with the computing device 100 such as the memory 132. In one embodiment, the memory 132 is part of the location device 300. In another embodiment, the memory 132 is in a separate computing device 100 with which the location device 300 is in communication. The communication may be accomplished in a variety of manners. In one example and not limitation, a thin optical fiber is used to communicate from the location device 300 to the computer 100. In another example and not limitation, the communication is accomplished wirelessly using virtually any frequency that is not harmful to a human. In yet another embodiment, the communication is accomplished using the strength of magnetic fields. Of course, many other methods of communication are possible and are contemplated.

At block 220, an additional location indication of the location device 300 may be received at an additional time mark. As previously explained, by receiving a plurality of location indications of the location device 300 at a plurality of times, movement of the location device 300 over time is possible. In addition, the time marks may be used to correlate with other outside and inside influences that are occurring at the time mark. For example, a test subject may be lifting an object at a specific time mark and information about the location of the location device 300 at the same time mark may be especially useful.

At block 230, the additional location indication and additional time mark may be stored in the memory 132 in communication with the computing device 100. By storing the location indication and time mark, the location indication and time mark may be further studied and analyzed. The location indication and time mark may be stored in a database or in any other appropriate electronic memory scheme. In one embodiment, the computing device 100 is located separate from the location device and in another embodiment, the computing device 100 is located within the location device 300. In one embodiment, the location device 300 data and time mark data may be stored in a memory 132 and may be downloaded to the computing device 100 at a later time. In another embodiment, the location device 300 data and time mark data are communicated in "real time" or nearly real time such as when the data is stored in the memory 132, it is then promptly communicated to the computing device 100.

Statistical analysis may be performed on the data to ensure the data (location device and timing) is reliable. For example, false readings of position of the location device 300 may be eliminated through statistical analysis. The data may be manipulated to be exportable to a plurality of illustration and data analysis programs.

Figure 4:
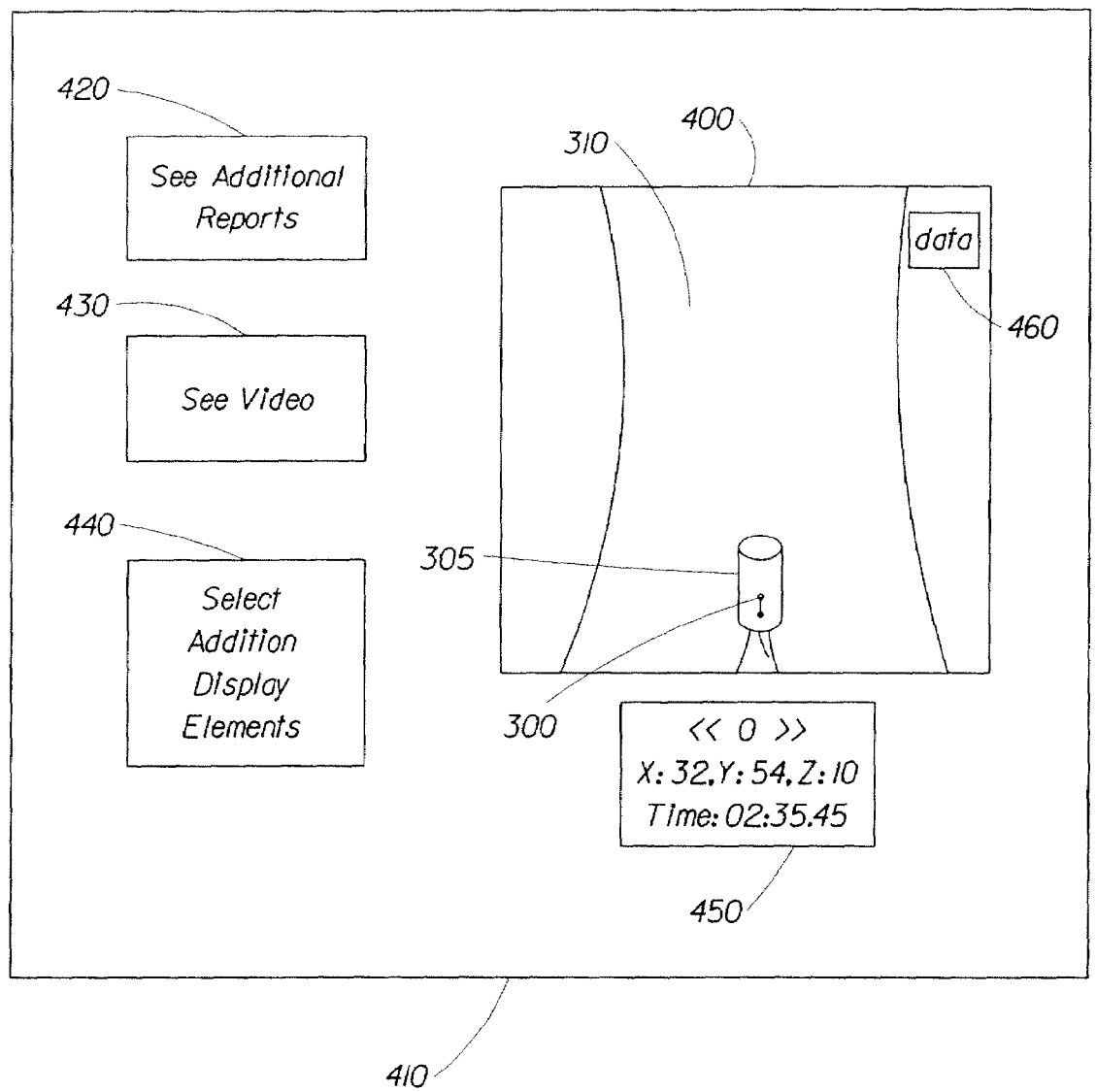
FIG. 4 is an illustration of a user interface that displays positional data related to the location device associated with the protection device.

At block 240, a report 400 may be created that illustrates the received location indication at the time mark and the received additional location indication at the additional time mark in the memory 132 in communication with the computing device 100. FIG. 4 is an illustration of one potential report 400. The report 400 may be displayed on a user interface 410 that displays several options 420, 430, 440 related to the time marks and the location indications such as adding in what a user was doing at each time mark, what a user was feeling at each time mark, such as, e.g., a wetness feeling, an uncomfortable feeling, or other feelings, adding a pulse rate to the report, etc. In certain embodiments, the report 400 can be in numerical form and/or graphical form. In addition, or alternatively, the report 400 can be a visual representation, such as, e.g., a two-dimensional representation, a three-dimensional representation, and/or a four-dimensional representation.

Figure 5:
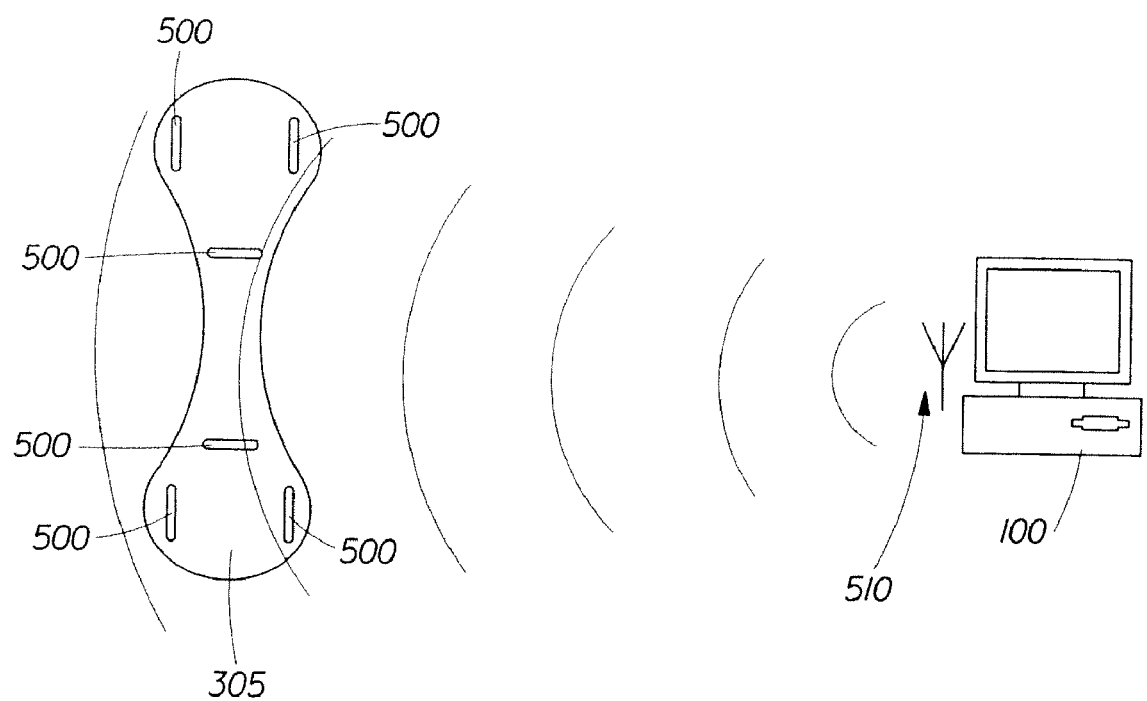
FIG. 5 is an illustration of first location device, a second location device, and a computing device.

In one embodiment, the location indication is analyzed to determine an interpreted location of a protection device 305 in relation to a human body 310. The location indication may simply be an indication of how the location indicator relates to another object such as a human body 310. The computer system 100 may take the location indication and, with previous knowledge or obtained knowledge about the subject human 310 or a representative human being, plot the location of the location indicator in view of the human body. FIG. 5 may be such an illustration. In yet another embodiment, the location indication and additional location indication along with measurement data about the human being 310 may be analyzed to determine an interpreted location of a protection device in relation to a human body 310. As yet another example and not limitation, the location indication may provide a GPS type signal that indicates the location of the location device 300.

In addition, the location indication may be interpreted across additional dimensions. For example, the location indication interpretation may place the location device in three dimensions in relation to a three dimensional representation of a human being, such as, e.g., the human being 310 in question. Software applications may be used to smooth the transitions from a first interpreted location to an additional interpreted location. In addition, as previously explained in relation to time marks, the location of the location device may stored and plotted over a number of time periods.

The report created 400 may be a three dimensional illustration of a human being and the location of the location device over a period of time. The illustration may be rotated through all three dimensions (x, y, z) and the position of the location device 300 or protection device 305 may also be illustrated in three dimensions. In addition, the illustration may be a video that illustrates the position of the location device 300 or protection device 305 over a period of time, such as, e.g., during one or more body movements of a human body, such as when the human body reaches down to lift a box or sit in a yoga position. Using start, stop, forward and reverse controls 450, the video 400 may be stopped and rotated in three dimensions and then started again.

As previously mentioned, the location device 300 may take on a variety of forms. By way of example and not limitation, FIG. 5 illustrates that the location device 300 may be one or more first location devices 500 associated with the protection device and a second location device 510 at a location remote from the first location. The location indication may compare a indication of a first location device 500 in relation to a second location device 510 where the second location device 510 is remote from the first location device 500. In some embodiments, the second location device 510 is located at a fixed position on the human being 310, such as, e.g., the coccyx, pubis, cervix, perineum, and/or an ilius of the pelvis, and in other embodiments, the second location device 410 is at a fixed location near the human being 310. When placed on the human body 310, a location that is relatively rigid such as the coccyx, may be a useful location for the second location device 510.

In operation, the first location device 500 may provide signals in response to communications from the second location device 510. The second location device 410 may create a magnetic field and may receive a response from the first location device 500 in response to the magnetic field. This response is interpreted into a location. Of course, other suitable methods of establishing the position of the first location device 500 in relation to the second location device 510 can be used. In certain embodiments, the location device 300 can be an electromagnetic device. In addition, or alternatively, in certain embodiments, the position of the location device 300 is not determined using ultrasound, Magnetic Resonance Imaging (MRI), or Computed Tomography (CT or CAT) scan.

In addition, the location device 300 may take on other forms and use different technology. For example, the location device 300 may be made up of a plurality of gyroscopes that communicate a plurality of individual location indications. In another example, the location device 300 may be a plurality of accelerometers that communicate a plurality of individual location indications. In a further example, the location device 300 may be a plurality of proximity detectors that communicate a plurality of individual location indications.

The location indications may be received periodically, such as at least about every 0.5 second, such as, e.g., at least about every 1 second. In other embodiments, locations are only communicated when the position of the location device 300 has moved more than a limit, such as 5.0 mm. In addition, the accuracy of the location indication may be +/−5.0 mm but, of course, this is just an example and not a limitation.

Data about the specific human body 310 in question may be gathered in a variety of ways. MRI, ultrasound, or x-ray may be used in advance to determine physical dimensions of the human being 310. Physical measurements also may be taken. Additional second location devices 510 may be place on parts of the body 310 itself in order accurately obtain the desired human 310 dimensions in three dimensions. Such second location devices 510 may be thought of as reference points. Any suitable points of attachment on the human body 310 for the reference second locations devices 510 can be used, such as, e.g., places that are relatively stable, such as the coccyx, the perineum and under the cervix of the human body 310. In addition, first location devices 500 that are attached to less stable places such as the buttocks may be used to determine the movement of the less stable places during movements and actions. Additional data 460 such as pressure data may be used to gather additional knowledge, such as, e.g., information related to how tight a protection device 305 is in a particular space, for example.

By knowing the specific location at which the location device 300 was installed in the protection device 305 (5 mm from perimeter for example), some measurement information about the human body 310 in question and the actual location of the location device 300, mathematics may be used to determine the location of protection device 305, where the protection device 305 is in relation to the human body 310 and/or the location of the location device 300 itself. By knowing the location of the protection device 305 in relation to the human body 310, information on problems such as protection device 305 leaks may be obtained.

Additional data 460 may also be received from the protection device 305. In one embodiment, a video device is also associated with, such as, e.g., installed in, the protective device 305 and video signals are received from the device. Time marks may also be stored with the video signals so that the video signals may be matched with the location indications. The video signals and time marks may be stored in a memory 132 and the video may also be displayed alone of with the location indication such as in FIG. 5. Steps also may be taken to synchronize the video time mark with the time mark and displaying a user interface in which both the video at the video time mark and location of the protection device at a same time mark are displayed.

As another example of the additional data 560 that may be available, pressure indications from a pressure sensor associated with the protection device 305 may be received. The pressure indications and at least one pressure time mark may be stored in the memory 132 in communication with the computing device 100. The pressure time mark with the time mark may be synchronized and displayed on a user interface in which the pressure indication and location of the protection device at a same time mark are displayed either alone or together or in combination with other relevant data. The pressure sensor may be a load cell, a stress strain gauge, a pressure sensor or any other appropriate pressure sensing device.

In addition, additional data 460 in the form of moisture indications from a moisture sensor associated with the protection device 305 may be received. The moisture indications may be stored in the memory 132 in communication with the computing device 100 and at least one moisture time mark in the memory 132 in communication with the computing device 100. The moisture time mark may be synchronized with the time mark and the moisture indication and location of the protection device at a same time mark may be displayed on a user interface, either alone, in combination or with other relevant information. The moisture can be natural moisture from the human being 310, such as, e.g., urine or menstrual fluid, or can be moisture introduced into the body. The moisture may be introduced by any suitable manner, such as, e.g., by providing a catheter on or into the body, and/or by using a catheter like device implanted into the protection device 305.

Additional data in the form of physical sensations 460 may also be received from the human being 310. The sensations may be stored and a sensation time mark may also be stored. The sensation time mark and the time mark may be synchronized such that the sensations may be displayed at the same time as the location indications. Of course, other relevant data may also be displayed. The sensations may include such sensations as cramping, wetness, heaviness, looseness, pressure, highness/lowness of the protection device 305 and leaking.

As discussed herein, indications of the location of location device 300 and/or protection device 305 may be collected during one or more body movements of the human being. The one or more body movements can be any suitable body movements, such as, e.g., voluntary body movements, such as, e.g., gross body movements, such as, e.g., movement of the whole body, movement of large segments of the body, use of large muscles, such as, e.g., leg muscles, arm muscles, and/or abdominal muscles. In certain embodiments, the one or more body movements do not include involuntary movements such as reflex movements, breathing, or other involuntary movements.

In certain embodiments, indications of the location of location device 300 and protection device 305 may be collected when the human being is in a certain position. Some example positions include a sitting position, a squatting position, a stretching position, a crawling position, a lifting position, a standing position, yoga positions and horizontal positions. The method may also track the position of the location device 300 and protection device 305 when there are transition movements from one position to another. In certain embodiments, the human being may be in a supported position, such as, e.g., supported by an object, such as, e.g., a table, a chair, or a bed. Alternatively, the human being may be in an unsupported position. In certain embodiments, the human being may be in an unsupported position during at least part of the body movements, such as, e.g., when transitioning from a seated position to a standing position.

The method may also track additional data 460 such as actions taken by the human 310 and store an action time mark such that the actions may be compared with the location device 300 during the action. The actions could be any actions of interest. For example and not limitation, the actions may include coughing, sneezing, running, lifting, defecating, urinating, walking, laughing, jumping, squatting, jogging, running, sprinting, swimming, performing yoga and playing a sport. The method may also track the position of the location device 300 when the human 310 has transition movement, such as, e.g., when the human 310 switches from one action to another action or from one position to a new action or from an action to a position.

As can be appreciated, numerous applications are available for the described system. In one embodiment, the protection device 305 may be a tampon and measurements may be taken to establish the position of the tampon in the vagina (FIG. 5). The tampon removal string may be marked with measurement markings to establish an initial position of the tampon using the measuring markings. This embodiment is especially unique because the location device 300 is inside the body yet in some embodiments, has no wires, which makes the human being feel more natural and able to provide one or more body movements for study.

The method may be used to create a user interface 410 (FIG. 4) for a computing device for displaying the location of the protection device 305 for a human being 310 and additional related data over a period of time. The interface 410 may display an illustration 400 of a location of a location device 300 and protection device 305 in relation to a human body 310 at a first point in time. The user interface 410 may also display a location of the location device 300 associated with the protection device 305 in relation to the human body 310 at a second point in time. The illustration 400 may also highlight the changes from the first point in time to the second point in time. The illustration 400 may include an animation of the movement of the location device 300 from the first point of time to the second point of time.

The user interface 410 may also display one or more options 420, 430, 440, 460 to obtain additional information related to the human body 310. The additional information available 460 may be displayed at the first point in time and at the second point in time. The moving illustration of movements may be updated at least once every 0.5 seconds based on location device 300 responses received and the location device 300 may be displayed with +\−5 mm of accuracy.

The additional data 560 may be a variety of data. For example and not limitation, the data 560 may include data about pressure on the protection device 305 received from a pressure sensor that is part of the protection device 305, video from a video device installed in the protective device 305, moisture readings from a moisture sensor installed in the protective device 305, physical sensations indicated by human being 310 such as cramping, wetness, heaviness, looseness, pressure, highness/lowness of protection device 305 and leaking. The additional data 460 may also include displaying the location of the protection device 305 when the human being 310 is in a position such as a sitting position, a squatting position, a stretching position, a crawling position, a standing position, a lifting position, a yoga position and a horizontal position. Further, the additional data 460 may include the location of the protection device 305 when the human being 310 is performing an action selected such as coughing, sneezing, laughing, running, jumping, squatting, defecating, urinating, lifting, walking, jogging, running, sprinting, swimming, performing yoga and playing a sport. The data 460 may also illustrate the location of the protection device 305 when the human being is transitioning from a first position to a second position, from a first action to a second action, from a first position to a first action, from a first action to a first position, etc.

By knowing the location of the protection device 305 during a plurality of times including the location of the protection device 305 in relation to the human 310 in question, the additional information at the same time marks may be studied to determine when and why protections devices move and potentially fail. By observing the movement of protection devices 305 dynamically or over a period of time in an unobtrusive but highly detailed way, additional insights may be gained into the movement, problems, failures and successes of protection devices 305. In addition, information may be learned how protection devices 305 deform and respond to a variety of factors and movements such that improved protection devices may be designed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of obtaining dynamic data related to a protection device worn by a human being during one or more body movements comprising:

Positioning the protection device within a vagina of the human being, wherein the protection device is selected from the group consisting of an absorbent article and a vaginal device;

Receiving at a computing device a device location indication of a first location device associated with the protection device during the one or more body movements at a device time mark;

Storing the device location indication and the device time mark in a memory in communication with the computing device;

Receiving at a computing device a body location indication of a second location device located at a position on the human being at a body time mark;

Storing the body location indication and the second time mark in a memory in communication with the computing device; interpreting the device location indication and body location indication along with measurement data about the human being to determine an interpreted location of the protection device within the vagina; correlating the device location indication and the body location indication to determine an occurrence when the protection device moves or fails;

Creating a report that illustrates the received device location indication at the device time mark and the received body location indication at the body time mark in the memory in communication with the computing device.

2. The method of claim 1, wherein the device time mark and the body time mark are substantially the same.

3. The method of claim 1, further comprising:

Receiving an additional device location indication of the first location device during the one or more body movements at an additional device time mark;

Storing the additional device location indication and additional device time mark in the memory in communication with the computing device;

Receiving an additional body location indication of the second location device during the one or more body movements at an additional body time mark; and Storing the additional body location indication and additional body time mark in the memory in communication with the computing device.

4. The method of claim 3, further comprising creating a report comprising an illustration of the movement of the device location indication from the device time mark to the additional device location at the additional device time mark and the movement of the body location indication from the body time mark to the additional body location at the additional body time mark.

5. The method of claim 1, wherein the one or more body movements are gross body movements.

6. The method of claim 1, wherein the first location device and the second location device are electromagnetic devices.

7. The method of claim 1, wherein the body location device is associated with a coccyx, a pubis, a cervix, a perineum, and/or an ilius of the pelvis of a human being.

8. The method of claim 1, further comprising receiving an indication of the location of the protection device when the human being is in a position selected from a group of positions comprising:
   Sitting position;
   Squatting position;
   Stretching position;
   Crawling position;
   Lifting position;
   Standing position;
   Yoga positions; and
   Horizontal position.

9. The method of claim 1, further comprising receiving an indication of the location of the protection device when the human being is performing an action selected from a group of actions comprising:
   Coughing, sneezing, running, lifting, defecating, urinating, walking, laughing, jumping, squatting, jogging, running, sprinting, swimming, performing yoga and playing a sport.

10. The method of claim 1, further comprising receiving an indication of the location of the protection device when the human being is transitioning from a first position to a second position where the first position and second position are selected from a group comprising:
   Sitting position;
   Squatting position;
   Stretching position;
   Crawling position;
   Standing position;
   Lifting position;
   Yoga positions; and
   Horizontal position.

* * * * *